United States Patent [19]

Beard

[11] Patent Number: 4,947,856
[45] Date of Patent: Aug. 14, 1990

[54] FLUID PRESSURE MONITORING AND FLOW CONTROL APPARATUS

[75] Inventor: Robert W. Beard, Placerville, Calif.

[73] Assignee: Abbott Laboratories, Abbott Park, Ill.

[21] Appl. No.: 262,887

[22] Filed: Oct. 26, 1988

[51] Int. Cl.$^5$ .......................................... A61B 5/0215
[52] U.S. Cl. .................................... 128/673; 128/748; 604/246; 604/256; 251/331
[58] Field of Search .................. 128/672–675, 128/748; 604/30, 32–34, 246–249, 256, 236–238; 251/331, 61.1; 137/510

[56] References Cited

U.S. PATENT DOCUMENTS

| | | | |
|---|---|---|---|
| 3,675,891 | 7/1972 | Reynolds et al. | 128/673 X |
| 4,341,224 | 7/1982 | Stevens | 128/673 X |
| 4,509,946 | 4/1985 | McFarlane | 128/673 X |
| 4,537,387 | 8/1985 | Danby et al. | 604/249 X |
| 4,576,181 | 3/1986 | Wallace et al. | 128/675 |
| 4,624,662 | 11/1986 | Le | 128/675 X |
| 4,638,811 | 1/1987 | Bisera et al. | 128/673 |
| 4,645,496 | 2/1987 | Oscarsson | 128/673 |
| 4,648,868 | 3/1987 | Hardwick et al. | 128/675 X |
| 4,703,759 | 11/1987 | Merrick et al. | 128/673 |
| 4,739,770 | 4/1988 | Stephens et al. | 128/675 |

Primary Examiner—Angela D. Sykes
Attorney, Agent, or Firm—Christensen, O'Connor, Johnson & Kindness

[57] ABSTRACT

Apparatus for monitoring fluid pressure and controlling fluid flow in a fluid line. The apparatus (10) includes a base (36) and a cover (38), between which is captured a membrane (42). The base includes an inlet port (18), a first outlet port (20), and a second outlet port (34). Channels formed within the base and covered by the membrane connect the inlet and outlet ports in fluid communication. The apparatus includes a flushing flow control valve (30) formed by a flow control projection (70), which projects outwardly from the base through the cover, and separates an inlet channel (62) from an outlet channel (64). A capillary flow passage 88 for restricting flow through the apparatus is disposed between the inlet channel and outlet channel comprises a capillary groove (86), formed across the flow control projection, adjacent the overlying membrane. Flushing fluid flow through the apparatus is obtained by pulling upwardly on a grip (90) to deform the membrane away from the flow control projection, thereby enlarging the capillary flow passage.

A pressure sensing assembly (28) is mounted on the apparatus in fluid communication with the outlet channel for continuous monitoring of fluid pressure. A flow direction valve is formed by a generally "T"-shaped flow direction channel (122) formed in the base and overlying the membrane, with an actuator button (128) being slidably secured to the cover above the flow direction channel providing for selection of the flow path. An inwardly extending valve projection (130) included on the actuator button bears on and deforms the membrane into the flow direction channel. Sliding the actuator button between three positions causes the membrane to selectively block one of the inlet or outlet ports, preventing fluid flow through that port, but allowing fluid flow between the other two ports.

18 Claims, 4 Drawing Sheets

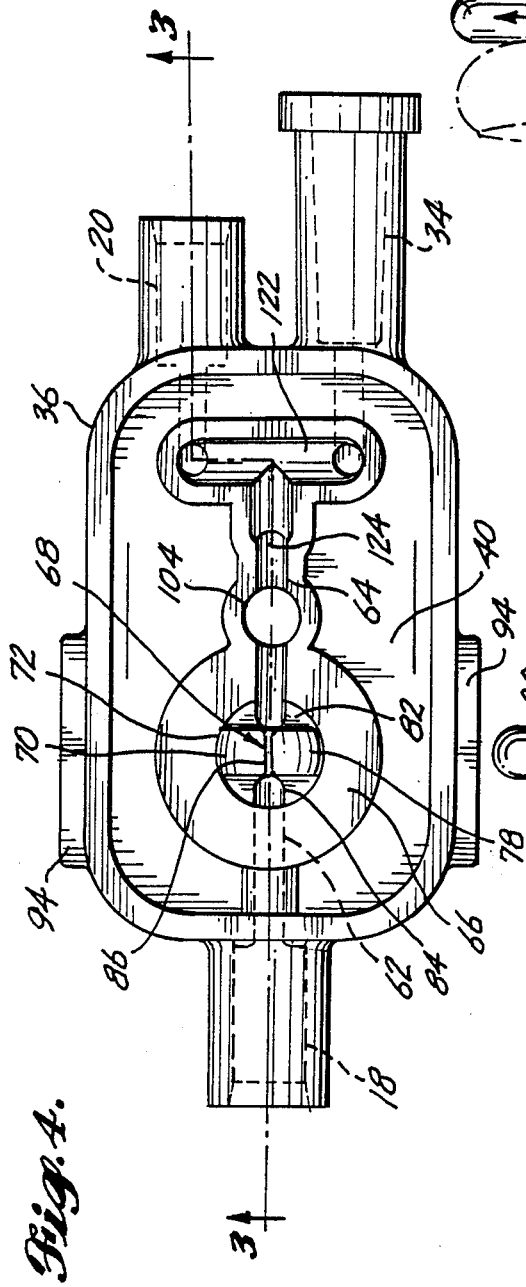

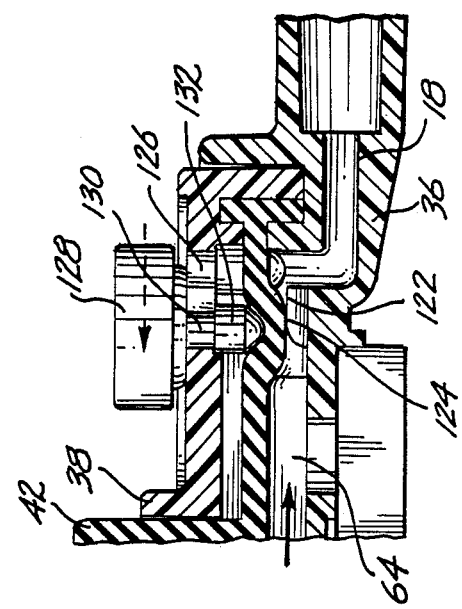
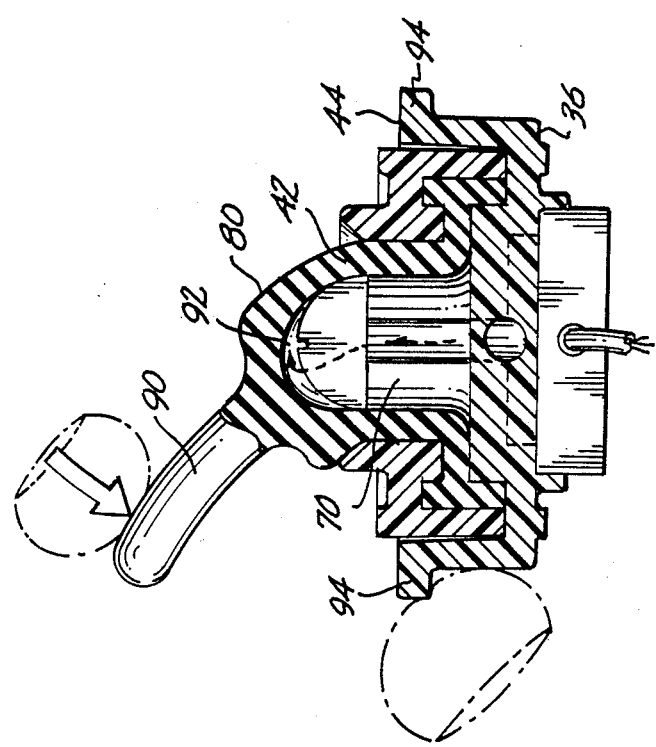

FLUID PRESSURE MONITORING AND FLOW CONTROL APPARATUS

TECHNICAL FIELD

The present invention relates to an apparatus for monitoring fluid pressure and controlling fluid flow in a fluid line, and more particularly, to an apparatus combining a flush valve, blood pressure transducer, and flow direction control valve.

BACKGROUND OF THE INVENTION

It is often desired to monitor the blood pressure of a patient to determine the patient's medical condition, and particularly to detect cardiovascular system stress. Blood pressure is often monitored invasively by inserting a catheter into a patient's vein or artery, with the open end of the catheter exposed to the pressure of the patient's circulatory system. The catheter is connected to a fluid line leading from a source of sterile solution that fills the fluid line and catheter. A fluid pressure sensing device, typically a pressure transducer, is connected in fluid communication with the line to sense the patient's blood pressure, which is transmitted by the fluid to the pressure transducer. The pressure transducer varies an electrical signal in proportion to the patient's blood pressure, and the electrical signal is monitored to detect changes in the patient's condition. Typically, a very low flow rate of solution passes through the fluid line and pressure transducer to clear away thrombi and minute air bubbles that would distort the pressure reading.

Blood pressure monitoring apparatus usually include a flush valve, disposed upstream of the pressure transducer, for controlling the rate of fluid flow through the device. The flush valve typically contains a capillary flow passage that restricts flow to a desired low rate. Before the fluid line is first connected to the patient, it is often desirable to greatly increase the flow rate of solution passing through the device to clear the line and device of air. Flush valves generally have a flushing position, bypassing the capillary passage, which permits this greatly increased flow through the device. Flushing is also periodically performed on a momentary basis while the fluid line is connected to the patient to clear thrombi, which may have accumulated within the line and device.

In addition to the flush valve, blood pressure monitoring apparatus may include a flow direction valve, which can be used to select one of three fluid flow conditions: (a) enabling normal flow through the device; (b) shunting fluid from the patient through a vent; and (c) blocking the flow of fluid into the device to prevent the fluid from entering the patient, thereby permitting other medication to be introduced into the catheter or fluid to be withdrawn from the patient through the catheter.

In recent years, apparatus combining a flush valve, a pressure sensing device, and a flow direction valve have been developed in a relatively low cost disposable format, which eliminates the need to sterilize the apparatus for reuse with other patients, and eliminates the risk of transmission of infectious disease caused by improper sterilization. Due to competition between manufacturers, it is desirable for these disposable devices to be as low in cost as possible, yet reliable, compact and simple to use.

Kodama et al., U.S. Pat. No. 4,683,894, discloses a disposable physiological pressure sensing device which attempts to meet these goals. The device includes a conventional three position stop cock valve for flow direction control, a pressure transducer, and a flush valve. The flush valve consists of a cylindrical valve body seated within a pressure chamber and sealed by an O-ring seal. The valve body includes a capillary bore passing through it that restricts fluid flow to a low rate for normal operation. The valve body is withdrawn from the chamber by pressing a lever on the device, which unseats the O-ring seal, and creates a bypass flow passage between the valve body and chamber for greatly increased flushing flow through the device.

While this device is disposable, its manufacture requires the assembly of many parts, raising the per unit cost. Rotation of the stop cock valve to change flow direction is a two-handed operation, which can be awkward for a health professional treating a patient in an emergency medical situation. Additionally, since activating the flush valve creates a bypass passage around the capillary bore formed in the valve body, the capillary bore is not flushed of any air or other contaminants that may be collected therein.

Other conventional blood pressure monitoring apparatus use a flush valve having an elastomeric valve body that is seated within the device, and which restricts normal flow to a capillary passage within the apparatus. The elastomeric valve body is deformed to open a second and larger bypass passage. One example of such a flush valve is shown in von Berg, U.S. Pat. No. 4,696,305, which discloses a device with interconnected parallel flow passages. One flow passage contains a capillary bore for normal flow through the device. The second and larger passage is closed by a thimble-shaped elastomeric valve body located within and sealing that passage. A plunger inserted within the valve body is depressed to open this second or flushing passage, causing the valve body to elongate and narrow to allow fluid flow through the passage. Again, since this device creates a bypass flushing flow, the capillary flow passage is not flushed to clear it of air or other contaminants.

SUMMARY OF THE INVENTION

The present invention discloses an apparatus with integral flow direction valve, pressure transducer, and flushing flow control valve that is directed towards solving the problems of the aforementioned prior art devices. The apparatus includes a housing having a base, a cover, and a flexible membrane sandwiched therebetween. The base includes an inlet port at one end that is connectable to a fluid line leading from a fluid source, and a first outlet port at the other end that is connectable to a catheter leading to a patient. The base also includes a second outlet port in proximity to the first outlet port for venting the apparatus. The upper surface of the base includes channels formed therein connecting the inlet and outlet ports in fluid communication. The flexible membrane overlies the upper surface of the base and covers the channels to create flow passages through the device, with the cover being secured to the base to seal the membrane to the base.

The inlet port is in fluid communication with an inlet channel included in the upper surface of the base. The inlet channel connects to a flow control channel, which in turn connects to an outlet channel that is in fluid communication with the first and second outlet ports.

The base includes a flow control projection which extends outwardly from the flow control channel, separating the inlet channel and the outlet channel. The flow control projection has a sealing surface across which is formed a capillary groove connecting the inlet channel to the outlet channel. The flow control projection protrudes through a flow control aperture included in the cover. The membrane includes a dome-shaped portion which covers and seals the sealing surface of the flow control projection, forming a capillary flow passage with the capillary groove. For normal operation of the device, fluid flow is restricted to a low flow rate through the capillary passage. A grip extending outwardly from the upper surface of the membrane can be grasped by a user to distort the membrane away from the flow control projection, enlarging the capillary flow passage to form a flushing flow passage to permit a greatly increased flow of fluid through the device. The membrane and flow control projection thus form a flushing flow control valve, which when activated not only flushes the overall device and fluid line, but also flushes the capillary passage.

The base also includes a pressure monitoring aperture opening into the outlet channel. A pressure sensing device, preferably a pressure transducer assembly, is mounted within and sealed to the pressure monitoring aperture to permit monitoring of the patient's blood pressure.

The base, membrane, and cover also form a flow direction valve. The outlet channel is connected by an interior port to one leg of a generally "T"-shaped flow direction channel. The remaining two legs of the flow direction channel are connected to the first outlet port and second outlet port. The flow direction channel is sealed by the overlying membrane, and a "T"-shaped slot is included in the cover directly above the flow direction channel. An actuator is slidably secured to the cover, and includes a projection extending inwardly into the flow direction channel. The projection terminates in a tip that bears upon the membrane and deforms the membrane into the flow direction channel. The actuator is slidable between three positions. In the first position, the membrane is deformed to block the interior port leading into the flow direction channel, preventing incoming flow from the solution source, but allowing flow between the first outlet port and second outlet port. In a second position, the membrane blocks the first outlet port, permitting flow only from the inlet port of the device to the second outlet port. In a third position, the membrane blocks the second outlet port, permitting flow only from the inlet port to the first outlet port.

The pressure monitoring and flow control device of the present invention is constructed by assembling the base, membrane, cover, and actuator. This simple construction reduces assembly cost of the device, making it an ideal disposable device. Both the flow control valve and the flow direction valve are easily actuated with one hand, freeing the other hand for performing other medical tasks.

BRIEF DESCRIPTION OF THE DRAWINGS

The present invention will now be described in greater detail, by way of example, with reference to the accompanying drawings in which:

FIG. 3 is a side elevation view of the apparatus in staggered cross section showing the flow control valve in its capillary configuration;

FIG. 4 is a top elevation view of the base illustrating flow channels and ports;

FIG. 5 shows a break away cross-sectional view of the flow control valve in the flushing configuration as actuated by pulling upward on the grip;

FIG. 6 is a break away cross section showing the flow control valve in the flushing configuration as actuated by squeezing the grip towards actuating flanges; and FIG. 7 is a break away cross-sectional view showing the flow direction valve in its first deformed configuration.

DETAILED DESCRIPTION OF THE PREFERRED EMBODIMENT

Figure 1:
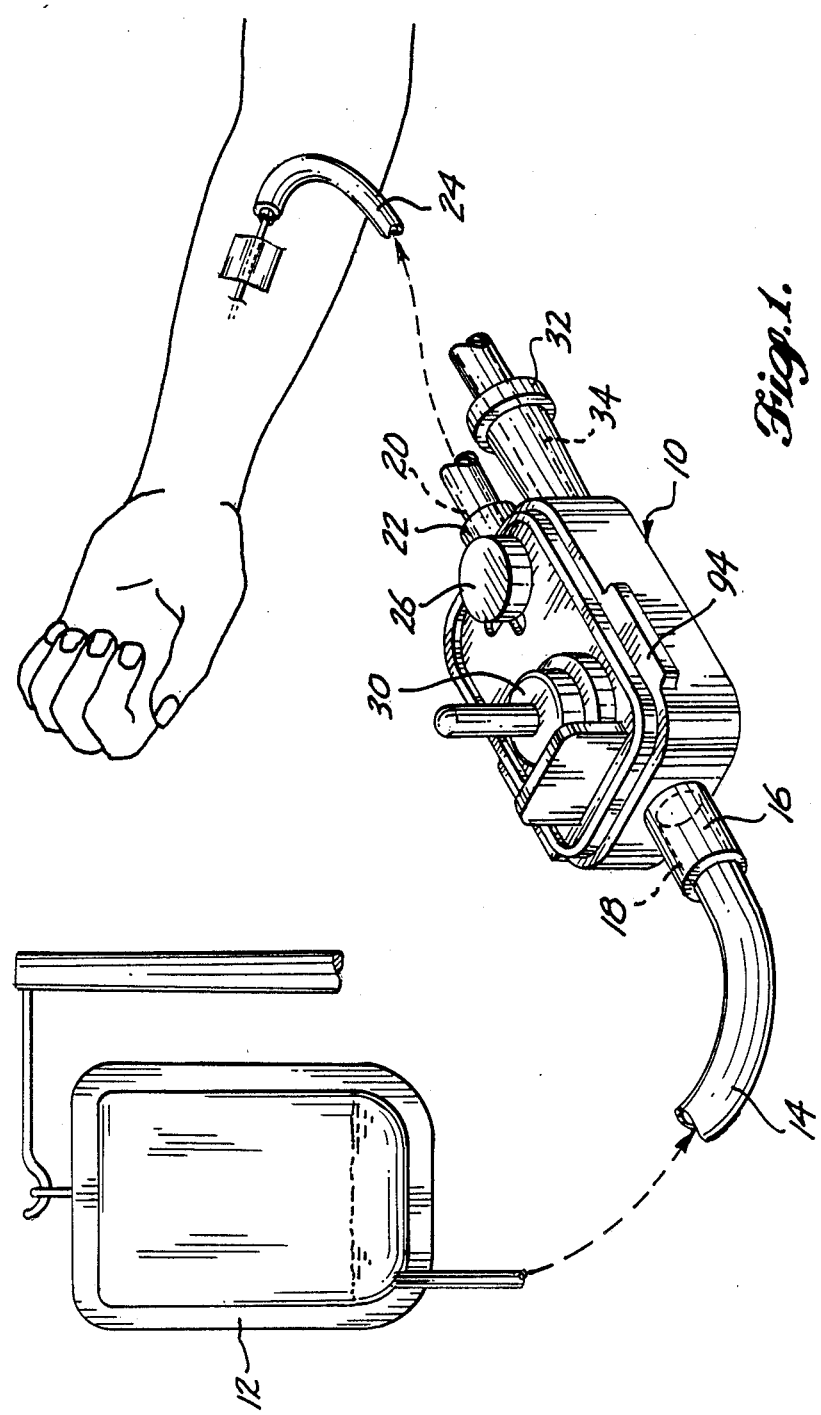
FIG. 1 illustrates the fluid pressure monitoring and flow control apparatus connected to an intravenous line and a patient catheter.

The preferred embodiment of a fluid pressure monitoring and flow control apparatus 10 is shown connected within a fluid line in FIG. 1. A fluid such as sterile saline solution flows from a reservoir 12 through an inlet line 14 that is connected to an inlet connector 16 included on apparatus 10. Fluid flows through the apparatus into a catheter 24, connected to an outlet connector 22 included on apparatus 10, for administration to a patient. As the fluid flows through the apparatus, it passes from an inlet port 18 formed within inlet connector 16, through an integral flushing flow control valve 30, past a pressure sensing assembly 28, through an integral flow direction valve 26, and exits through a first outlet port 20 formed within outlet connector 22.

The device also comprises a vent connector 32, including a second outlet port 34 formed therein. In the preferred embodiment, inlet connector 16 and outlet connector 22 are friction-fit tubing connectors, although other types, such as luer connectors could be used. Vent connector 32 is illustrated as a luer connector; it may be connected to a waste line to receive fluid vented from the inlet line, or to a fitting to permit the injection of medications into the fluid line connected to the patient. The illustrated configuration of the apparatus, including one inlet and two outlets, represents a preferred configuration, but the present invention also encompasses apparatus with only one outlet, or with additional inlets and outlets, as desired for specific applications.

Figure 2:
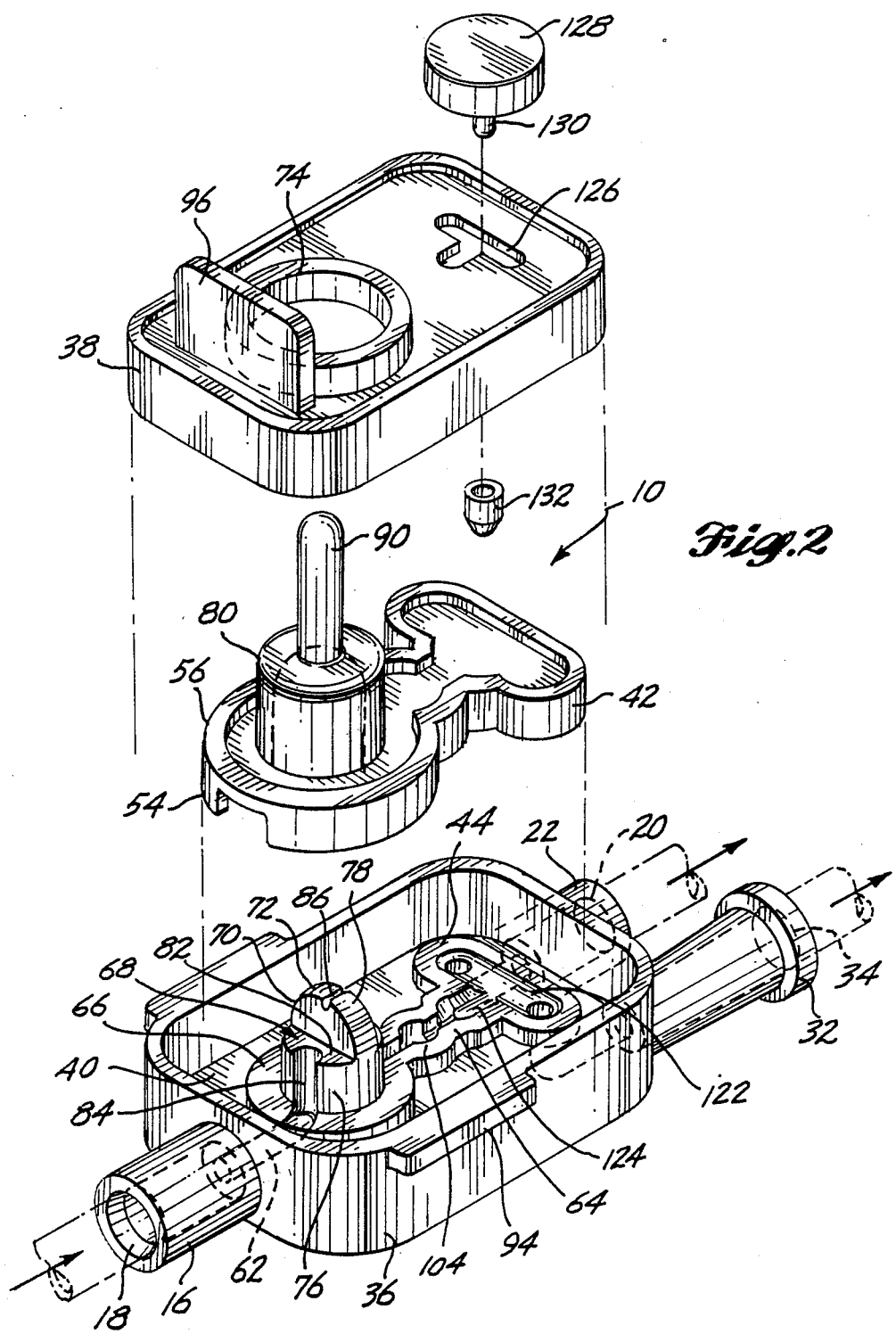
FIG. 2 is an isometric exploded view of the apparatus.

Turning to FIG. 2, which shows an exploded view of the preferred embodiment of the invention, apparatus 10 includes a housing comprising a base 36 and a cover 38. Base 36 includes connectors 16, 22, and 32 and ports 18, 20, and 34. Base 36 has an upper surface 40, which includes channels formed therein connecting inlet port 18, first outlet port 20, and second outlet port 34 in fluid communication. A membrane 42 overlies upper surface 40 of base 36, covering the flow channels to form fluid flow passages between the ports. Membrane 42 is captured between base 36 and cover 38, sealing membrane 42 to upper surface 40 of base 36. Base 36 and cover 38 are preferably formed of a tough, rigid plastic such as polycarbonate, although other suitable materials such as nylon or stainless steel could be used. Membrane 42 is preferably formed of a resilient, flexible material such as silicon rubber.

Peripheral sealing of membrane 42 between base 36 and cover 38 is insured by providing flanges on each of these components. FIG. 3 shows assembled apparatus 10 in cross section and illustrates the interconnection of these components. Base 36 includes an upwardly projecting base flange 44 formed along its perimeter, and a base groove 46 formed within upper surface 40, just inside base flange 44. Cover 38 includes a downwardly projecting cover flange 48 formed along its perimeter, and a cover groove 50 formed within a lower surface 52 of cover 38, just inside cover flange 48. Membrane 42 includes a downwardly projecting lower sealing flange 54 and an upwardly projecting upper sealing flange 56 formed along the membrane's outer perimeter.

To assemble apparatus 10, the membrane is stretched slightly to allow insertion of the lower sealing flange 54 of membrane 42 within the base groove 46. An actuator button 128 for the flow direction valve 26, described below in greater detail, is then installed on cover 38. Cover 38 is then engaged with base 36, with sealing flange 56 of membrane 42 being inserted into cover groove 50. When so engaged, cover flange 48 is located inside base flange 44 and bears upon the bottom surface 60 of base groove 46. Membrane 42 is compressed slightly between base 36 and cover 38 to cover and seal upper surface 40 of base 36. To complete the assembly, cover 38 is secured to base 36. In the preferred embodiment, base 36 is secured to cover 38 by ultrasonic welding, although other methods may be used, such as securing them with an adhesive or threaded fasteners. Assembled base 36, membrane 42, and cover 38 cooperate to form flushing flow control valve 30, as will be apparent from the following description.

Referring to FIGS. 2 and 4, which show details of the channels and ports formed within base 36, it can be seen that inlet port 18 is in fluid communication with an inlet channel 62 and that outlet ports 20 and 34 are in fluid communication with an outlet channel 64. Inlet channel 62 is separated from outlet channel 64 by a flow control surface portion 66 of upper surface 40. A flow control channel 68 is formed within flow control surface portion 66, and connects inlet channel 62 with outlet channel 64. A flow control projection 70, having an outer sealing surface 72, extends upwardly from the center of flow control channel 68.

With reference again to FIG. 3, flow control projection 70 extends upwardly through a flow control aperture 74 included in cover 38. Flow control projection 70 of the preferred embodiment includes a cylindrical lower portion 76, terminating in a convex upper portion 78. Membrane 42 includes a dome-shaped portion 80, which covers sealing surface 72 of flow control projection 70 and blocks flow control channel 68.

Referring back to FIGS. 2 and 4, convex upper portion 78 of flow control projection 70 has two recessed shoulders 82 in proximity to the inlet channel 62 and the outlet channel 64. Two fluid flow grooves 84 are formed on either side of cylindrical lower portion 76 and connect recessed shoulders 82 to inlet channel 62 and outlet channel 64. Finally, a shallow "V"-shaped capillary groove 86 is formed across convex upper portion 78, between the two fluid flow grooves 84.

Capillary groove 86 and overlying membrane 42 thus define a capillary flow passage 88 connecting inlet channel 62 to outlet channel 64, as shown in FIG. 3. The relatively small cross section of capillary flow passage 88 restricts the flow of fluid through apparatus 10 to a low rate during normal operation of the apparatus.

Membrane 42 includes an integral cylindrical grip 90 projecting upwardly from its dome-shaped portion 80.

When grip 90 is grasped by a user and pulled upwardly, dome-shaped portion 80 of membrane 42 is distorted away from sealing surface 72 of flow control projection 70, as shown in FIG. 5. In this manner, membrane 42 is deformed from its normal capillary configuration to a flushing configuration, enlarging capillary flow passage 88 to form a flushing flow passage 92 between sealing surface 72 and membrane 42. Flushing flow passage 92 allows a greatly increased flow of fluid through apparatus 10, to flush the fluid line and the internal passages within the apparatus.

Base 36 includes two outwardly projecting gripping flanges 94, formed below and projecting perpendicularly from base flange 44, on either side of flow control projection 70. Membrane 42 may alternately be deformed to its flushing configuration by squeezing its dome-shaped portion 80 and grip 90 towards either one of gripping flanges 94, as illustrated in FIG. 6, resulting in enlargement of capillary flow passage 88 to form flushing flow passage 92. Cover 38 includes an upwardly extending guard projection 96 adjacent flow control aperture 74 (FIG. 3). Guard projection 96 extends slightly higher in elevation above base 36 than flow control projection 70, and is provided to prevent inadvertent deformation of membrane 42 to its flushing configurations e.g., in the event that a patient rolls onto apparatus 10.

Downstream of flushing flow control valve 30, the apparatus includes a pressure sensing assembly 28 that is in fluid communication with outlet channel 64, as shown in FIG. 3. Base 36 has a lower surface 100 that includes a rectangular pressure sensing recess 102 formed therein. A pressure monitoring aperture 104 is formed within pressure sensing recess 102, opening into outlet channel 64. In the preferred embodiment of the present invention, pressure sensing assembly 28 includes a conventional pressure transducer 106. A pressure sensitive surface 108 of the transducer is housed within a cavity 112 formed within a box-like transducer housing 110. Transducer housing 110 is inserted within the pressure sensing recess 102 of base 36, and includes an annular flange 114 that projects upwardly into engagement with pressure monitoring aperture 104.

Transducer housing 110 is sealed to base 36 by sonic welding, or alternatively with an adhesive. Pressure sensitive surface 108 of pressure transducer 106 is disposed below pressure monitoring aperture 104. A fluid interface 116 fills the cavity formed by flange 114, disposed above pressure sensitive surface 108. Fluid interface 116 transmits fluid pressure from outlet channel 64 to pressure sensitive surface 108, and also prevents direct contact of the fluid flowing through apparatus 10 with pressure sensing assembly 28. Silicon gel is a preferred material for fluid interface 116, although other interface materials may be used.

Pressure sensing assembly 28 produces an electrical output signal that varies in proportion to the fluid pressure applied to pressure transducer 106. The electrical output signal is transmitted over an electrical lead 118, to a monitor or recording device. Since outlet channel 64 is typically connected in fluid communication with the patient's circulatory system by first outlet port 20 and catheter 24, pressure sensing assembly 28 is typically used to monitor the patient's blood pressure.

The apparatus further includes a flow direction valve 26 (FIG. 1), which controls flow between the various ports by the interaction of base 36, cover 38, and membrane 42. Flow direction valve 26 is located downstream of pressure sensing assembly 28, and is in fluid communication with outlet channel 64 and first and second outlet ports 20 and 34 (FIG. 3). Flow direction valve 26 can selectively be placed in: a first position, in which it prevents fluid flow from inlet port 18 to either first outlet port 20 or second outlet port 34, but allows fluid flow between the first and second outlet ports 20 and 34; a second position, in which fluid flow is allowed only from inlet port 18 to second outlet port 34; and, a third position, in which fluid flow is allowed only from inlet port 18 to first outlet port 20.

In normal operation of apparatus 10, flow direction valve 26 is in its third position, enabling fluid flow from reservoir 12 through the apparatus and into the patient, as shown in FIG. 3. When it is necessary to purge the fluid line of air, such as during initial connection of the fluid line and intermittently during administration of fluid to the patient, flow direction valve 26 is placed in its second position so that all air and fluid in the line can be vented from the apparatus through the second outlet port 34 into a vent fluid receptacle. At other times during use of the apparatus, it may be desired to stop fluid flow into the patient without disconnecting catheter 24, or to introduce other medication into the fluid line for treatment of the patient, by placing flow direction valve 26 into its first position. As discussed above, apparatus 10 may alternately include fewer or more inlets and outlets, depending upon its required usage, and flow direction valve 26 can easily be modified so that it controls flow by being moved selectively between a number of different positions, each position corresponding to one of the ports in the apparatus, as will be apparent from the following description.

Flow direction valve 26 includes a generally "T"-shaped flow direction channel 122 formed within upper surface 40 of base 36, as shown in FIGS. 2 and 4. A first leg of the "T"-shaped flow direction channel 122 opens into outlet channel 64 through an interior port 124. Second and third legs of the "T"-shaped flow direction channel 122 open into first outlet port 20 and second outlet port 34, respectively. Membrane 42 covers flow direction channel 122, and cover 38 includes a generally "T"-shaped slot 126 disposed above flow direction channel 122 (FIG. 2). An actuator button 128 is slidably secured to cover 38 by a valve projection 130 that extends inwardly from actuator button 128 through slot 126. Prior to the assembly of cover 38 to base 36 a convex tip 132 is affixed to the inner extremity of the valve projection 130, slidably securing actuator button 128 to cover 38. Actuator button 128 is slid alternatively into one of the three legs of "T"-shaped slot 126 to place flow direction valve 26 in one of its three selectable positions. As actuator button 128 is moved, convex tip 132 bears and slides upon membrane 42, deforming the membrane into flow direction channel 122 to block that channel at a point immediately below tip 132.

When actuator button 128 is in its first position, tip 132 is located adjacent interior port 124, placing membrane 42 into its first deformed configuration to block that port as shown in FIG. 7. Actuator button 128 may also be slid to its second position, in which tip 132 is adjacent first outlet port 20, with membrane 42 being deformed to its second deformed configuration, blocking first outlet port 20. In the third position of the actuator button, tip 132 is adjacent second outlet port 34, with membrane 42 being deformed to its third deformed configuration, blocking second outlet port 34. In each of these three positions, one port is blocked to prevent fluid flow through that port, while allowing fluid flow between the two remaining unblocked ports.

OPERATION

The preferred embodiment of the fluid pressure monitoring and flow control apparatus 10 described above is used to monitor the blood pressure of a patient, but includes flushing flow control valve 30 and flow direction valve 26. Prior to using apparatus 10, inlet line 14 leading from the fluid reservoir 12 is connected to inlet connector 16, and catheter 24 is connected to outlet connector 22 (FIG. 1).

Flushing flow control valve 30 is normally in its capillary flow configuration, with dome-shaped portion 80 of membrane 42 covering and sealing flow control projection 70 within apparatus 10 (FIG. 3). When so configured, membrane 42 covers capillary groove 86, formed across flow control projection 70, defining capillary flow passage 88, which permits only a low flow rate of fluid through the apparatus.

Prior to inserting the catheter into a patient's vein or artery, the fluid line and apparatus 10 must be flushed of air. The apparatus is prepared for initial flushing by first placing flow direction valve 26 into its third position, in which tip 132 of actuator button 128 deforms the membrane 42 into flow direction channel 122 to block second outlet port 34. When flow direction valve 26 is in this position, fluid flows through the apparatus from inlet port 18 to first outlet port 20.

Flushing flow control valve 30 is then placed in its flushing configuration, either by pulling upward on grip 90 (FIG. 5), or by squeezing grip 90 and dome-shaped portion 80 of membrane 42 towards one of gripping flanges 94 included on base 36 (FIG. 6). Either of these actions causes membrane 42 to be deformed and distorted away from sealing surface 72 of flow control projection 70, enlarging capillary flow passage 88 to create flushing flow passage 92 between membrane 42 and flow control projection 70. A greatly increased rate of fluid flow is thus enabled through the apparatus to flush it and the connected fluid line of air.

Grip 90 is released to return flushing flow control valve 30 to its normal capillary configuration (FIG. 3); catheter 24 may then be inserted into the patient's vein or artery. The low rate of fluid flow permitted through the apparatus by the flushing flow control valve 30 while in its capillary configuration generally keeps the fluid line from becoming blocked with thrombi formed by clotting of the patient's blood. Connection of apparatus 10 in this manner places pressure sensing assembly 28 in fluid communication with the patient's blood stream for continuous monitoring of the blood pressure.

Despite the slow capillary flow of fluid through the apparatus, some thrombi may accumulate over time within the fluid line and within apparatus 10. To assure that this accumulation does not block the fluid line, flushing flow control valve 30 is occasionally momentarily placed in its flushing configuration to allow a brief surge of an increased flow rate of fluid through the device, flushing any thrombi located in the apparatus, including within capillary flow passage 88, back into the patient.

In some circumstances, it may be desired to flush apparatus 10 and inlet line 14 by venting fluid from the apparatus away from the patient and into a vent receptacle connected to second outlet port 34. To accomplish venting in this manner, flow direction valve 26 is placed in its second position by sliding actuator button 128 so that its tip 132 is adjacent first outlet port 20. In this position, tip 132 deforms membrane 42 so that it blocks fluid flow through first outlet port 20, yet permits fluid flowing through inlet port 18 to vent through second outlet port 34. Flushing flow control valve 30 is then again placed into its flushing configuration by pulling or squeezing grip 90 to allow a greater flow rate of fluid through apparatus 10. After venting is completed, grip 90 is released and flow direction valve 26 is returned to its third position, by appropriately repositioning actuator button 128.

Occasionally, it may also be desired to completely shut off inlet flow from fluid reservoir 12. To accomplish this function, flow direction valve 26 is placed in its first position, in which its tip 132 is adjacent interior port 124, deforming membrane 42 to block first interior port 124, thus stopping incoming fluid flow from inlet port 18 (FIG. 7). One instance in which flow from inlet port 18 is so blocked is to allow introduction of other medicinal fluids into the patient's circulatory system through second outlet port 34. A line from the other source of medicinal fluid is connected to vent connector 32, allowing the other medication to flow through that line, through apparatus 10, and into the patient. Alternatively, a septum (not shown) may be connected to vent connector 32, with medication being injected through the septum flowing into the patient through apparatus 10. Normal flow is recommenced by moving flow direction valve 26 to its third position.

After treatment of a patient is completed, apparatus 10 is disposed of. Due to its relatively low cost, the apparatus is not intended to be sterilized for reuse with other patients.

The preferred embodiment of the fluid pressure monitoring and flow control apparatus described above includes a base, a cover, and a single membrane. Other configurations of the present invention are possible within the scope of the claims that follow, such as apparatus comprising a separate membrane for use in the flow control valve, and in the flow direction valve, respectively. It may also be desired in some circumstances to construct an apparatus in accordance with the present invention that includes only a flushing flow control valve, or only a flushing flow control valve and a pressure sensing assembly, or only a pressure sensing assembly and a flow direction valve. The apparatus described above, which includes all three features in an integral combination, is described as a preferred embodiment of the present invention, but is not meant to limit the scope of the invention to only that combination.

The present invention also encompasses several alternative configurations for construction of the membrane and capillary groove flow control valve. Instead of the membrane covering a capillary groove formed across a flow control projection, the membrane may cover a capillary groove formed across a generally planar flow control surface portion, disposed on the upper surface of the base, to define the capillary flow passage. Further, the flushing flow control valve may comprise the membrane and a recessed capillary groove disposed within a concave flow control channel formed in the base, with the membrane being deformed into the concave flow control channel using a spring biased tip to cover the capillary groove, thereby defining the capillary flow passage. A plastic grip connected to the spring biased tip would be grasped and pulled to enlarge the passage, providing a flushing flow.

Finally, the flow direction valve can use depressable buttons mounted on the cover above the flow direction channel to deform the membrane into the channel for changing of valve positions, rather than the slidable actuator button described in the preferred embodiment.

While the present invention has been disclosed with respect to the preferred embodiment thereof, those of ordinary skill in the art will understand that further modification as to the invention, including but not limited to those described above, may be made within the scope of the claims appended below. Accordingly, it is intended that the scope of the invention should not be limited to what has been disclosed above, but instead should be determined entirely by reference to the following claims and equivalents thereof.

The embodiments of the invention in which an exclusive property or privilege is claimed are defined as follows:

1. An apparatus for monitoring fluid pressure and controlling flow in a fluid line, said apparatus comprising:
   (a) a base having an upper surface, an inlet port, and a first outlet port, said upper surface including a channel formed therein in fluid communication with said inlet port and said first outlet port, said inlet and first outlet ports being adapted to connect to the fluid line;
   (b) a flexible membrane having a planar configuration while relaxed, said membrane overlying the channel in said upper surface of said base, said membrane being resiliently deformable from the relaxed planar configuration to a deformed configuration in which said membrane is curvedly deformed to block fluid flow through said channel;
   (c) means for sealing said membrane to said upper surface of said base;
   (d) means for selectively deforming said membrane from its relaxed planar configuration to its deformed curved configuration; and
   (e) pressure sensing means in fluid communication with said channel for sensing fluid pressure in the fluid line, said pressure sensing means being disposed within said base.

2. The apparatus of claim 1, wherein:
   (a) said base includes a second outlet port in fluid communication with said channel; and
   (b) said membrane is selectively deformable from its relaxed configuration to:
      (i) a first deformed configuration, in which the membrane blocks said channel so as to prevent fluid flow from the inlet port to the first and second outlet ports, but permits fluid flow between the first and second outlet ports;
      (ii) a second deformed configuration, in which the membrane blocks said channel so as to permit fluid flow only from said inlet port to said second outlet port; and
      (iii) a third deformed configuration, in which the membrane blocks said channel so as to permit fluid flow only from said inlet port to said first outlet port.

3. The apparatus of claim 2, wherein:
   (a) said means for sealing said membrane comprise a cover having a lower surface and an upper surface, said cover being securable to said base, said membrane being disposed between the lower surface of said cover and the upper surface of said base, said cover including a slot disposed above the membrane and said channel; and
(b) said means for selectively deforming said membrane comprise an actuator slidably secured to the upper surface of the cover, said actuator including a projection extending inwardly through said slot, said projection having a tip that bears upon said membrane causing the membrane to deform and project into said channel, said actuator being slidable between:
  (i) a first position, in which the membrane is in its first deformed configuration;
  (ii) a second position, in which the membrane is in its second deformed configuration; and
  (iii) a third position, in which the membrane is in its third deformed configuration.

4. An apparatus for monitoring fluid pressure and controlling fluid flow in a fluid line, said apparatus comprising:
(a) a housing having an inlet port and an outlet port, said inlet and outlet ports being adapted to connect to the fluid line, a pressure monitoring aperture in fluid communication with said outlet port, a capillary flow passage connecting said inlet port in fluid communication with said outlet port, said capillary flow passage restricting fluid flow through the apparatus and the fluid line and being disposed within a non-planar and substantially curved surface of the housing;
(b) means for reversibly enlarging said capillary flow passage, permitting a greatly increased fluid flow through said apparatus to flush said capillary flow passage, said apparatus and the fluid line, said means being contoured to conform to the curved surface of the housing to define the capillary flow passage and to define an inlet passage and an outlet passage by covering open channels disposed on each side of the capillary passage; and
(c) pressure sensing means for sensing fluid pressure in the fluid line, said pressure sensing means being disposed within the housing and sealed to said pressure monitoring aperture.

5. An apparatus for monitoring fluid pressure and controlling fluid flow in a fluid line, said apparatus comprising:
(a) a base having an upper surface, an inlet port, and a first outlet port, said inlet and first outlet ports being adapted to connect to the fluid line, said upper surface including an inlet channel and an outlet channel formed therein, said inlet channel being in fluid communication with said inlet port and said outlet channel being in fluid communication with said first outlet port, said upper surface being non-planar and further including a substantially curved flow control surface portion separating said inlet channel and said outlet channel, said base including a capillary flow passage disposed in said curved flow control surface portion, connecting said inlet channel in fluid communication with said outlet channel, said base also including a pressure monitoring aperture in fluid communication with said outlet channel;
(b) a flexible membrane overlying and contoured to conform to the curved flow control surface portion of said base and in conjunction therewith defining parts of the inlet channel and of the outlet channel that are disposed on each side of the capillary flow passage by covering open portions of the inlet and outlet channels, said membrane being resiliently deformable between a capillary configuration and a flushing configuration;
(c) means for sealing said membrane to the upper surface of said base;
(d) first means for selectively deforming said membrane between its capillary configuration, in which said membrane seals against said flow control surface portion to permit fluid flow only through said capillary flow passage, and its flushing configuration, in which said membrane is distorted away from said flow control surface portion, creating a flushing flow passage between the membrane and the flow control surface portion to permit greatly increased fluid flow through the apparatus for flushing of the apparatus and the fluid line; and
(e) pressure sensing means for sensing fluid pressure in the fluid line, said pressure sensing means being disposed within and sealed to said pressure monitoring aperture.

6. The apparatus of claim 5, wherein said capillary flow passage comprises a capillary groove formed across said flow control surface portion, said capillary flow passage being enlarged to form said flushing flow passage when said membrane is resiliently deformed from its capillary configuration to its flushing configuration.

7. The apparatus of claim 6, wherein said means for sealing said membrane comprises a cover having a lower surface and an upper surface, said cover being securable to said base, said membrane being disposed between the lower surface of said cover and the upper surface of said base, said cover including a flow control aperture disposed above said flow control surface portion.

8. The apparatus of claim 7, wherein:
(a) said flow control surface portion includes a flow control channel formed therein in fluid communication with said inlet channel and said outlet channel, and a flow control projection extending outwardly from said flow control channel and through said flow control aperture, said flow control projection having a sealing surface, with said capillary groove being formed across said sealing surface; and
(b) said membrane covers said flow control projection and projects through said flow control aperture, with said membrane in its capillary configuration sealing against said sealing surface, permitting flow only through said capillary groove, and with said membrane in its flushing configuration being distorted away from said sealing surface, enlarging said capillary flow passage to form said flushing flow passage.

9. The apparatus of claim 8, wherein said first means for selectively deforming said membrane comprises a grip secured to said membrane, said grip being grasped by a user to distort said membrane away from said sealing surface of said flow control projection.

10. The apparatus of claim 9, wherein:
(a) said flow control projection includes an outwardly extending portion terminating in a convex portion; and
(b) said grip is flexible and formed integrally with said membrane, said grip projecting from said membrane, proximate the center of said convex portion of said flow control projection.

11. The apparatus of claim 9, wherein said base includes a second outlet port in fluid communication with said outlet channel, said apparatus further comprising valve means for selectively:
(i) allowing fluid flow between the first and second outlet ports;
(ii) allowing fluid flow from said inlet port to said second outlet port; and
(iii) allowing fluid flow from said inlet port to said first outlet port.

12. The apparatus of claim 11, wherein:
(a) said upper surface of said base further includes a flow direction channel formed therein, said first outlet port and second outlet port opening into said flow direction channel, said flow direction channel including an interior port connecting said flow direction channel in fluid communication with said outlet channel;
(b) said membrane overlies said flow direction channel and is selectively deformable from a relaxed configuration to a first deformed configuration, a second deformed configuration, and a third deformed configuration;
(c) said cover includes a slot disposed above the flow direction channel; and
(d) said valve means comprises second means for selectively deforming said membrane from its relaxed configuration to:
(i) its first deformed configuration, in which the membrane projects into said flow direction channel and blocks said interior port to prevent fluid flow through said inlet port;
(ii) its second deformed configuration, in which the membrane projects into said flow direction channel and blocks fluid flow through said first outlet port; and
(iii) its third deformed configuration, in which the membrane projects into said flow direction channel to block fluid flow through said second outlet port.

13. The apparatus of claim 12, wherein said second means for selectively deforming said membrane comprises an actuator slidably secured to the upper surface of the cover, said actuator including a projection extending inwardly through said slot, said projection having a tip that bears upon said membrane, causing said membrane to deform and project into said flow direction channel, said actuator being slidable between a first position, in which the membrane is in its first deformed configuration, a second position, in which the membrane is in its second deformed configuration, and a third position, in which the membrane is in its third deformed position.

14. The apparatus of claim 13, wherein said flow direction channel and said slot are generally "T" shaped.

15. The apparatus of claim 13, wherein said pressure sensing means comprise:
(a) a pressure transducer, said pressure transducer varying an electrical output signal in response to the fluid pressure within said outlet channel;
(b) a transducer housing forming a cavity in which the pressure transducer is disposed, said transducer housing having an engaging flange that connects with and seals to said pressure monitoring aperture of said base;
(c) a fluid interface disposed within said engaging flange for transmitting fluid pressure from said outlet channel to said pressure transducer; and
(d) an electrical interface for conveying electrical signals to and from said pressure transducer.

16. The apparatus of claim 15, wherein said cover includes a guard projection extending outwardly in proximity to said flow control aperture to prevent inadvertent deformation of said membrane.

17. An apparatus for controlling fluid flow in a fluid line, said apparatus comprising:
(a) a base having an upper surface, an inlet port, a first outlet port, and a second outlet port, said upper surface including a channel formed therein in fluid communication with said inlet, first outlet and second outlet ports, said inlet port and said first outlet port being adapted to connect to the fluid line;
(b) a flexible membrane overlapping said upper surface of said base, said membrane being resiliently deformable from a relaxed configuration to:
(i) a first deformed configuration;
(ii) a second deformed configuration; and
(iii) a third deformed configuration;
(c) means for sealing said membrane to said upper surface of said base; and
(d) means for selectively deforming said membrane from its relaxed configuration to:
(i) its first deformed configuration, in which the membrane blocks said channel so as to prevent fluid flow from the inlet port to the first and second outlet ports, but permitting fluid flow between the first and second outlet ports;
(ii) its second deformed configuration, in which the membrane blocks said channel so as to permit fluid flow only from said inlet port to said second outlet port; and
(iii) its third deformed configuration, in which the membrane blocks said channel so as to permit fluid flow only from said inlet port to said first outlet port.

18. The apparatus of claim 17, wherein:
(a) said means for sealing said membrane comprises a cover having a lower surface and an upper surface, said cover being securable to said base, said membrane being disposed between the lower surface of said cover and the upper surface of said base, said cover including a slot disposed above the membrane and said channel; and
(b) said means for selectively deforming said membrane comprises an actuator slidably secured to the upper surface of the cover, said actuator including a projection extending inwardly through said slot, said projection having a tip that bears upon said membrane causing said membrane to deform and project into said channel, said actuator being slidable between:
(i) a first position, deforming the membrane to its first deformed configuration;
(ii) a second position, deforming the membrane to its second deformed configuration; and
(iii) a third position, deforming the membrane to its third deformed position.

* * * * *